Figure 1:
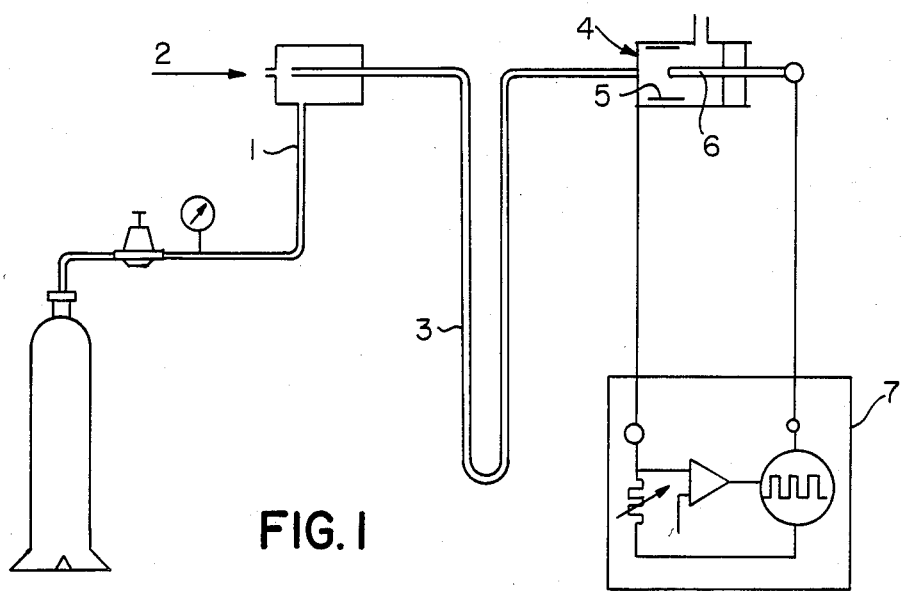

United States Patent [19]

Mendes

[11] Patent Number: 4,680,472

[45] Date of Patent: Jul. 14, 1987

[54] PROCESS AND APPARATUS FOR THE STABILIZATION OF MEASURING RESULTS FURNISHED BY AN "ELECTRON CAPTURE" DETECTOR WITH IDENTIFICATION OF ANOMALIES AFFECTING THE DETECTOR

[75] Inventor: Claude Mendes, Yerville, France

[73] Assignee: Giravions Dorand, Suresnes, France

[21] Appl. No.: 818,635

[22] Filed: Jan. 14, 1986

[30] Foreign Application Priority Data

Jan. 14, 1985 [FR] France ................................. 85 00423

[51] Int. Cl.$^4$ ............................................. G01N 27/66
[52] U.S. Cl. ................................... 250/386; 250/382; 250/379
[58] Field of Search ............... 250/374, 386, 384, 382, 250/381, 379; 324/464, 465, 130; 73/23.1

[56] References Cited

U.S. PATENT DOCUMENTS 3,361,908  6/1968  Petitjean et al. .................... 250/381

OTHER PUBLICATIONS

Landowne, R., "Optimum Current Concept in the Operation of Electron Capture Detectors", Analyt, Chem., vol. 42, No. 12 (1970).

Primary Examiner—Carolyn E. Fields
Assistant Examiner—Richard Hanig
Attorney, Agent, or Firm—Millen & White

[57] ABSTRACT

When using an electron capture detector for the molecular identification of electrophilic compounds, the sensitivity of the detector is made reproducible by controlling the voltage or frequency of the pulses applied to it to maintain a reference current whose set value is produced automatically by the device after determination of the characteristics of the state of the detector, namely a so-called saturation current CM and a so-called spontaneous current CS, according to a law of proportionality between these two currents.

In addition, knowledge of these state characteristics gives information on the physical and physicochemical anomalies of the analysis device having an effect on the sensitivity of the detector, and consequently enables them to be remedied.

8 Claims, 4 Drawing Figures

PROCESS AND APPARATUS FOR THE STABILIZATION OF MEASURING RESULTS FURNISHED BY AN "ELECTRON CAPTURE" DETECTOR WITH IDENTIFICATION OF ANOMALIES AFFECTING THE DETECTOR

Considering by way of non-limiting example the chromatographic analysis of a gas-phase mixture, said analysis consisting of introducing a vaporized sample, by means of a gas stream, to the interior of a tube or "column", the sample will have a characteristic separation according to the passage through the column of the components of the sample mixture introduced, which components issue from the column in an order whose chronology is dependent on their molecular nature.

The marking and relative determination of the components are obtained at the exit of the column by means of a detector sensitive to the passage of a single molecule or several together.

There are numerous detection methods for these molecules, and the corresponding detectors each have their particular area of application for which they are suitable. One of these, the Electron Capture Detector, is based on the ability of certain molecules to capture free electrons, and the electrical detection and quantification of the capture date indicates the presence and amount of these molecules. For this purpose, a potential difference is applied between the body of the detector and a measuring electrode located in the gaseous flow in order to collect the free electrons present, and the current obtained is measured. The gas flows there through a cell which is exposed to an ionizing source.

When an electrophilic compound passes through the detector, it captures the free electrons to form negative ions, the geometry of the detector being optimized so that the remaining free electrons are collected and that the ions formed are not collected, or are less collected. The reduction in the population of free electrons results in a reduction in the collected current.

The free electrons necessary for the detection are obtained, for example, by means of a slightly radioactive source (tritium or nickel 63) or by any other known means of producing $\beta$ radiation which, bombarding the molecules of the vector gas, releases by collision a plasma of positive ions, raadicals and low energy free electrons.

The potential difference enabling the collection of the free electrons and giving the measure signal can be fixed DC or controlled variable DC, or pulsed at a fixed frequency or pulsed at a controlled variable frequency, the control having to maintain the collected current constant. When there is no control, the measurement of the variations in the capture current quantitatively characterizes the intensity of the electron capture in the detection chamber and consequently the presence and amount of electrophilic molecules with respect to the pure vector gas.

In fact, most existing detectors use a pulsed power supply at controlled variable frequency for dynamic measuring range reasons. The current coming from the detector is then compared with a fixed reference current, and the frequency of the pulses is controlled by closed loop to maintain the collected current at the value of this reference. It is therefore the measurement of the resultant variations in the frequency or in the analogical voltage controlling this frequency which gives quantitative information on the presence of the electrophilic compounds passing through the detector.

However, experience shows that an ideal analysis system (total absence of leakages, perfectly pure carrier gas, perfectly clean column and detector, noncontaminating injected produces) does not exist and that the characteristics of a detector can change causing a drift in the sensitivity.

A first object of the present invention is to make the sensitivity of an electron capture detector, powered with controlled variable DC voltage or controlled modulated frequency voltage, reproducible. A second object is to enable the identification of the origin of anomalies coming from the analysis device and liable to influence the functioning of the detector (leakages, fouling, purity of carrier gas, etc).

An electron capture detector according to the invention, for measuring the presence of an added component in a vector gas, comprises means to apply a voltage to a measuring electrode in contact with said gas in a cell exposed to an ionizing source, means to vary said voltage in value or pulse frequency to maintain the current collected by said electrode equal to a constant reference current, and means to use said varying voltage as a measure signal, further comprises means to set said reference current according to a law of proportionality intermediate between a maximum current and a spontaneous current at the ends of a useful linear curve section determined by preliminary measurements carried on the pure vector gas.

In a preferred embodiment the detector further comprises means to display the results of said preliminary measurements in terms of said maximum current, said spontaneous current and the slope of said linear curve section.

Thus in a gas analysis process of the invention, wherein said gas comprises at least one added component in a vector gas, said process being used, in particular, in gas chromatography analysis, the process comprises introducing said gas in a cell exposed to ionizing radiations, said cell being the chamber of an electron capture detector as described herein above.

Before a series of analysis measurements, preliminary measurements are carried on the pure vector gas for determining the curve of the variations of the variable voltage signal with respect to the current, determining therein an useful linear curve section and at the ends of it the values of the maximum current and the spontaneous current. The reference current for the measurements on the gas mixture to be analyzed is set according to the law of proportionality previously selected by the user.

Thus if CM is the maximum current (or saturation limit current) and CS the spontaneous current, the reference current CR is automatically set by the electronics associated to the detector according to the formula:

$$CR - CS = m (CM - CS)$$

The factor m can be given any suitable constant value between 0 and 1.

A device for analyzing a gas mixture according to the invention will preferably include a computer with a program for calculating automatically the values of the maximum current CM, the spontaneous current CS and optionally the slope P of the linear curve section CS-CM.

In practice the preliminary measurements and calculation of the reference current value CR are made rather often between different chromatograms when the device has been recently installed, until a steady state is obtained for the values of CS, CM and P.

Then the same measurements are repeated from time to time and at least when there is some important change in the operating conditions, for instance when connecting a new supply of the vector gas or when the operating temperature is changed, or the detector has been let to cool temporarily.

Another important feature of the invention is that abnormal operation can be known by observing the values obtained by the preliminary measurements.

There can be thus detection of the anomalies of the emitting source, of the type and of the flow rate of the carrier gas, of the temperature and of the state of contamination of the detector by the variations in the saturation or maximum current CM, the anomalies in the state of oxidation of the detector by the variations in spontaneous current CS, and the anomalies in the cleanliness of the carrier gas by the variations in the slope P of the curve of the variation in the voltage value or frequency applied to the detector.

It will be understood that the electronics associated to the detector can preferably comprise means for storing the current values and voltage values (of the voltage itself or of the frequency of voltage values) obtained during the preliminary measurements, means to determine therefrom the useful linear section, the spontaneous current CS for a zero voltage (or frequency), the value of the maximum current CM and means to calculate the value of a reference current CR according to the formula $$CR - CS = m(CM - CS)$$

wherein m is a constant between 0 and 1.

In such a device, one can make use of means for an incremental scanning of the current up to saturation, means of measuring the maximum current CM taking, for example, as a value for CM, that of the current at the last increment before saturation.

A device according to the invention can include means for determining the curve of voltages or frequencies as a function of the current and means of deducing the slope P of that curve.

It can further comprise means of displaying the values of the maximum current CM, the spontaneous current CS and the slope P of the curve of variations in the voltage or frequency of the power supply current as a function of the current.

It is generally advantageous that a device according to the invention should include means of triggering on demand the means of measuring, of display and of calculating according to a predetermined program.

The invention will be better understood from reading the following detailed description and from examining the appended drawings which show, by way of non-limiting example, an embodiment of the invention.

Figure 2:
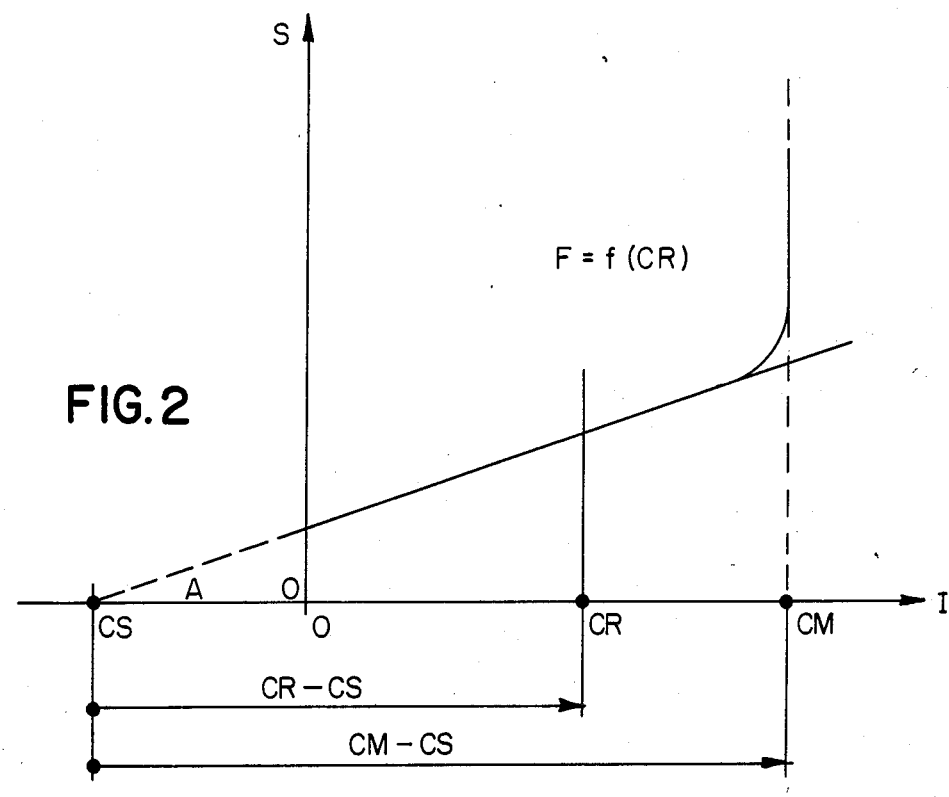
Figure 3:
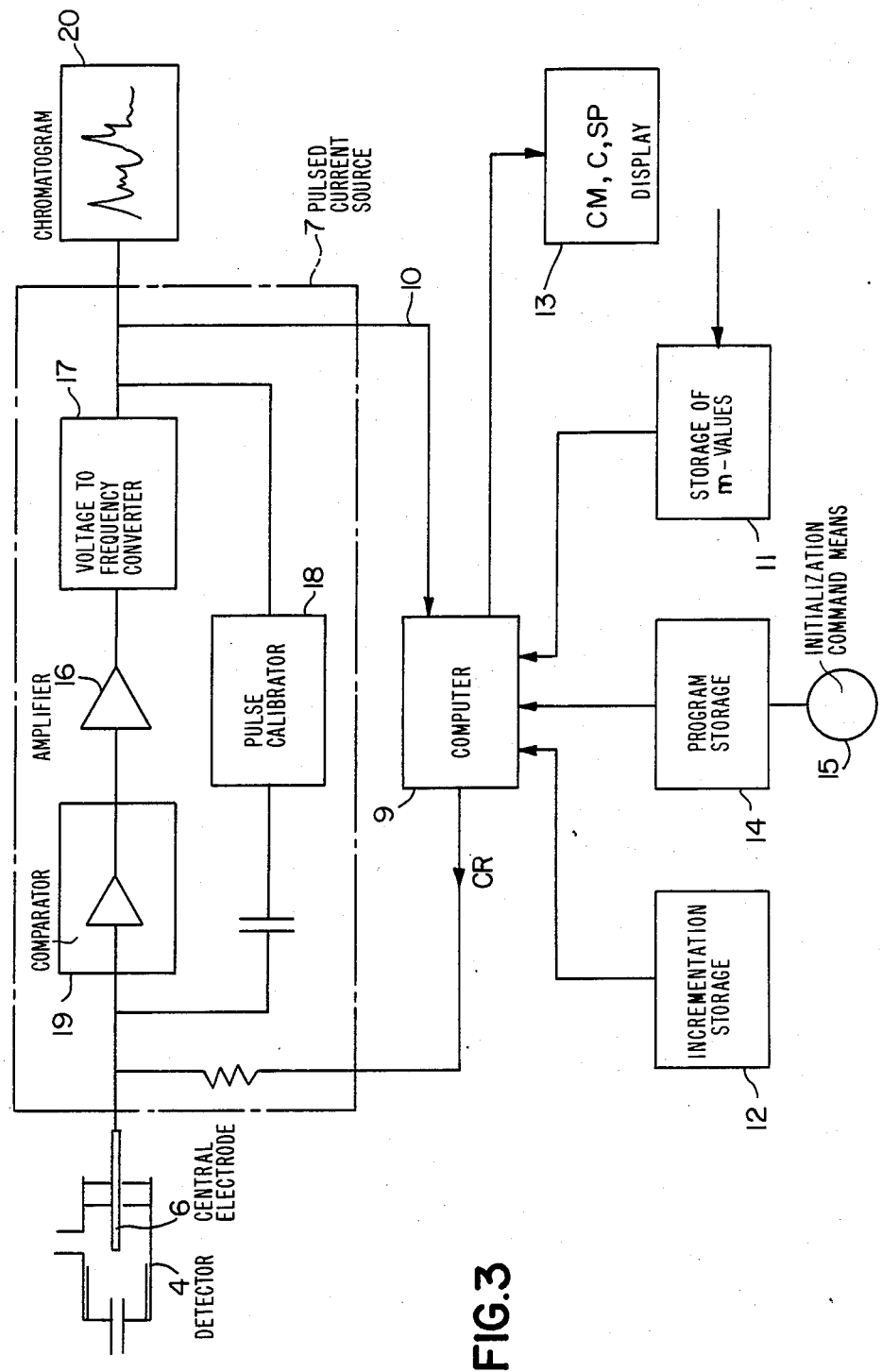
Figure 4:
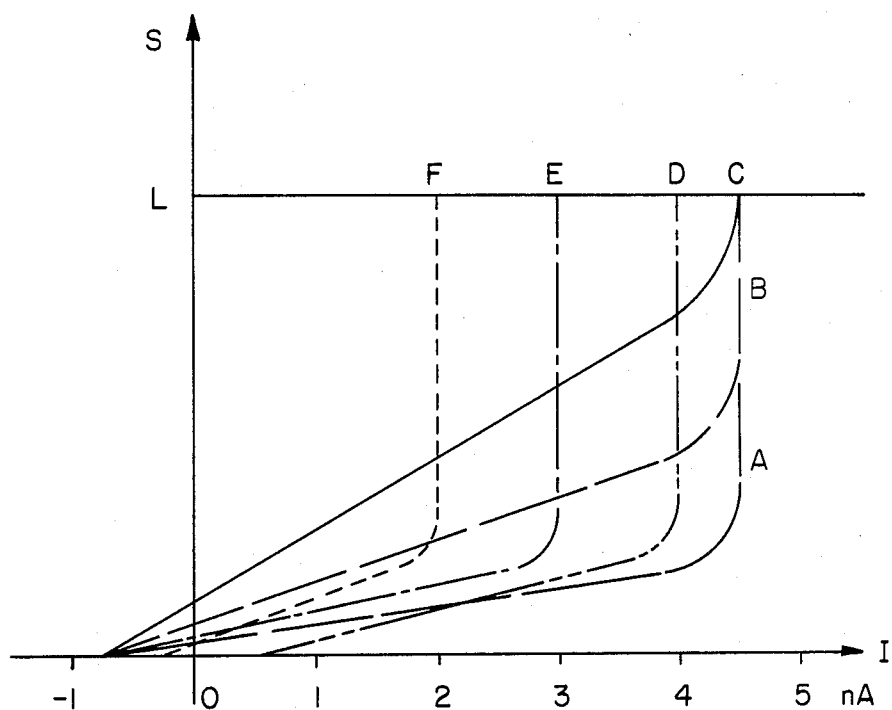

In these drawings:

FIG. 1 diagrammatically represents a gaseous phase chromatographic analysis installation with an electron capture detector, FIG. 2 is a diagram representing the signal obtained (controlled DC voltage or controlled frequency) as a function of the set current of this control, FIG. 3 is a block diagram of the device controlling the frequency of the measuring current in an analysis system having a controlled frequency according to the invention, FIG. 4 is a diagram showing the interpretations that can be made from the measurement of the currents CM and CS and of the slope P.

In the device shown in FIG. 1, the carrier gas is let in at 1, the sample is taken in and vaporized in 2 in order to then pass through the "column" 3. The detector 4 is installed at the output of the column, its inside wall has received the radioactive source 5 and a central electrode 6 enables the draining of a measuring current from a modulated frequency generator 7 whose frequency is forced to maintain the current passing through at a preset reference value. The changes in this frequency are read in order to characterize the sample.

The diagram of FIG. 2 shows a curve of the variations of the voltage signal in view of the current measured as obtained when performing the preliminary measurements using the pure vector gas.

The curve shows a linear section before the signal increases rapidly at a so-called saturation zone. In some instances it is also possible to measure the spontaneous current CS for a null signal when it has a positive value. When its value is negative as shown in the drawing, it is determined from the extrapolation of the linear section. The value of the maximum current CM is that formed at the saturation zone.

When some compound is present in the vector gas, the curve will vary. According to the invention the signal will be measured while the current is maintained at a constant value which is set at a reference current value CR calculated as a function of CM and CS following the relationship:

$$CR - CS = m (CM - CS)$$

where m is a constant between 0 and 1.

This permits to ensure the reproducibility of the sensitivity of the detection. That means that from a series of measurements to another one, provided that the reference current is set as above, the signal height will always indicate the same amount of molecules detected.

The practical limits in the choice of the coefficient m depend on the equipment and the mode of operation and in any case m will be chosen in order to have a positive current CR that is sufficiently distant from the saturation and the spontaneous current CS.

In the diagram of FIG. 3, the detector 4 is powered by the pulsed current source 7 whose frequency is controlled by slaving the delivered current to the reference value CR as set by the computer 9;

It is more precisely shown that the voltage signal passes through a comparator 19, then it is amplified in 16 and converted in a voltage frequency by a voltage frequency converter 17 before being recorded as a chromatogram in 20.

The reference 18 shows a signal treatment device for calibrating the pulses of the voltage.

The value CR results from a computation carried out by the block 9 from knowledge of the frequency at 10 and the coefficient of proportionality m displayed in 11, the incrementation being produced in 12; CR is not therefore a value that is displayed contrary to that which it is usual to find in current installations.

The values CM, CS and P are displayed in 13. The program 14 imposes the succession of these operations starting from an initialization command 15 available to the operator.

The display, according to the invention, of the values CM, CS and P also enables the interpretation of abnormal or drifting values which give information on the nature of the physical and physicochemical anomalies that can affect the analysis system and cause appreciable variations in the sensitivity of the electron capture detector.

In fact it has been noted that:

CM depends on the energy of the electrons emitted in the capture chamber, on the nature and the flow rate of the carrier gas, on the temperature and on the state of contamination of the detector, but depends only slightly on the cleanliness of the carrier gas.

CS mainly depends on the state of oxidation of the emitting source of the detector, P depends on the state of cleanliness of the carrier gas.

It is thus possible to identify the anomalies in the analysis system by cross-checking the abnormal or drifting measurements of CM, CS and P and consequently to remedy them.

In a specific embodiment the device may include alarms for indicating such anomalies in particular the alarm system may be operated when the value of CM comes down to a minimum value.

In the diagram of FIG. 4, several examples of curves have been shown, representing the signal obtained (controlled voltage or controlled frequency) as a function of the applied current, the currently encountered numerical values having been chosen by way of non-limiting example for the abscissas in order to take better account of the identification of the anomalies. Curve A characterizes a detector in good condition working with a clean analysis system and an uncontaminated gas. If the contamination in this gas increases slightly, we obtain curve B, and we obtain curve C if this contamination becomes very high. On the other hand, if the carrier gas contains traces of oxygen, we note on curve D an oxidation of the detector as CS moving towards positive values which can be made to fluctuate by the oxygen contribution resulting from a backward diffusion at the level of upstream leakages. If CM decreases according to curve E, it is probably because the carrier gas has carried traces of contaminants masking the activity of the emitting source. CM will decrease further if the internal energy of this source decreases and curve F is obtained. Experiences enables many other interpretations to be made and it is clear that the measurement and the display of the characteristics CM, CS and P form an advantageous means of detecting the anomalies of the analysis system and consequently of correcting them.

The invention is of course in no way limited to the described and represented embodiment; it is capable of numerous variants accessible to a specialist in the field, depending on the envisaged applications and without falling thereby outside the scope of the invention.

Thus, it would be possible to measure or calculate CM, CS and P by other methods resulting from the definition of these values according to FIG. 2, for example by applying a current scanning searching a field including all possible curves and giving a voltage or frequency peak for CM and a zero frequency or voltage for CS, these investigations also being controlled by a sequential program subsequently calculating and displaying CR.

All the operations can be automatically carried out by appropriate circuits within the system, the result being the production and use of the measurement of the reference current and the display of the values CM, CS and P for the purpose of diagnosing the anomalies of the analysis system.

What is claimed is:

1. An electron capture detector for measuring the presence of an added component in a vector gas comprising means for applying a voltage to a measuring electrode source, means for varying said voltage in value or pulse frequency to maintain the current collected by said electrode equal to a constant reference current, and means for using the varying voltage as a measurement signal; said detector further comprising means to set said reference current according to a law of proportionality intermediate a maximum current and a spontaneous current at the ends of a useful linear curve section of a current curve determined by preliminary measurements carried on a pure vector gas.

2. A detector according to claim 1 further comprising means to display the results of said preliminary measurements in terms of said maximum current, said spontaneous current and the slope of said linear curve section.

3. A method for measuring the presence of an added component in a vector gas using an electron capture detector and for stabilizing the sensitivity of the detector in a series of measurements, comprising performing a preliminary series of measurements with the pure vector gas determining therefrom a maximum current or saturation limit current CM and a spontaneous current CS for a zero (voltage value or frequency) signal, determining a reference current CR higher than CS of an amount proportional to the difference CM−CS according to the relationship $CR - CS = m \ (CM - CS)$ where m is a predetermined constant number between 0 and 1, then performing said series of measurements by measuring the collected current issued from the detector, comparing the value measured to the value of said reference current CR and modifying the voltage (voltage value or pulse frequency) supplied to the detector so as to maintain the collected current equal to the reference current.

4. Automatic device programmed to stabilize the measurements provided by an electron capture detector powered with controlled continuous supply current or with controlled modulated frequency pulsed supply current, characterized in that it includes an electron emitting source, means for measuring the voltage value or frequency of the power supply current, means for measuring the spontaneous current CS of the detector as a positive value, means for measuring a spontaneous current CS at zero frequency or for calculating the spontaneous current when having a negative value (by storage of prior measurements), means for measuring a saturation current CM of the detector, means for determining the value of a reference current CR by computation according to the formula:

$$CR - CS = m(CM - CS)$$

where m is a constant between 0 and 1, and means for applying this reference current CR to control the voltage or frequency of the supply current.

5. A device according to claim 4, characterized in that the means for measuring the frequency comprises means for an incremental scanning of the supply current up to saturation, and in that the means for measuring the saturation current CM take as a value for CM that value of the supply current at the last increment before saturation.

6. A device according to claim 4, characterized in that it includes means for determining the curve of the voltage or frequency as a function of the reference current CR and means for deducing the slope P of that curve.

7. An automatic device according to claim 4 including means for displaying the saturation current CM, the spontaneous current CS and the slope P of the curve of variations in the voltage and frequency of the power supply current as a function of the current.

8. A device according to claim 7, including a means for triggering the displaying means and means for calculating the spontaneous current according to a predetermined program.

* * * * *